United States Patent
Minnigh et al.

(10) Patent No.: US 8,351,568 B2
(45) Date of Patent: Jan. 8, 2013

(54) LONG LENGTH MULTIPLE DETECTOR IMAGING APPARATUS AND METHOD

(75) Inventors: Todd R. Minnigh, Pittsford, NY (US); Timothy J. Wojcik, Rochester, NY (US)

(73) Assignee: Carestream Health, Inc., Rochester, NY (US)

( * ) Notice: Subject to any disclaimer, the term of this patent is extended or adjusted under 35 U.S.C. 154(b) by 231 days.

(21) Appl. No.: 12/557,839

(22) Filed: Sep. 11, 2009

(65) Prior Publication Data
US 2011/0064193 A1 Mar. 17, 2011

(51) Int. Cl.
*G01N 23/083* (2006.01)
*H05G 1/02* (2006.01)

(52) U.S. Cl. ............ 378/62; 378/55; 378/204

(58) Field of Classification Search ........... 378/51, 378/55, 62, 68, 91, 96, 98, 98.8, 98.12, 114, 378/145–147, 150, 189, 204, 206, 210
See application file for complete search history.

(56) References Cited

U.S. PATENT DOCUMENTS

| | | |
|---|---|---|
| 4,613,983 A | 9/1986 | Yedid et al. |
| 5,111,045 A | 5/1992 | Konno et al. |
| 5,123,056 A | 6/1992 | Wilson |
| 5,130,541 A | 7/1992 | Kawai |
| 5,986,279 A | 11/1999 | Dewaele |
| 6,807,250 B2 * | 10/2004 | Wang et al. .................. 378/63 |
| 6,895,076 B2 | 5/2005 | Halsmer et al. |
| 6,944,265 B2 | 9/2005 | Warp et al. |
| 7,177,455 B2 | 2/2007 | Warp et al. |
| 7,265,355 B2 | 9/2007 | Chang et al. |
| 7,555,100 B2 | 6/2009 | Wang et al. |
| 2005/0129298 A1 | 6/2005 | Warp et al. |
| 2008/0152088 A1 * | 6/2008 | Wang et al. .............. 378/98.12 |

FOREIGN PATENT DOCUMENTS
EP 0 919 856 A1 6/1999

OTHER PUBLICATIONS

Commonly assigned U.S. Appl. No. 12/538,930, filed Aug. 11, 2009, titled "Retrofitable Long-Length Digital Radiography Imaging Apparatus and Method," Todd R. Minnigh, et al.

* cited by examiner

Primary Examiner — Anastasia Midkiff

(57) ABSTRACT

An apparatus for obtaining a long length x-ray image of a subject has a first x-ray detector, a second x-ray detector, and an x-ray source having an exposure directing apparatus that is actuable to direct exposure from the x-ray source towards at least a first imaging position during a first interval and a second imaging position during a second interval, with an overlap along a boundary between the at least first and second imaging positions. An x-ray detector holder has a detector translation apparatus that is actuable to translate at least one of the first and second x-ray detectors to an interim position for one of the first and second intervals and to either the first or the second imaging position for the other of the first and second intervals. A host controller is programmed to provide instructions for movement of the x-ray detector holder and exposure directing apparatus.

20 Claims, 16 Drawing Sheets

LONG LENGTH MULTIPLE DETECTOR IMAGING APPARATUS AND METHOD

FIELD OF THE INVENTION

The invention relates in general to digital radiographic imaging, and in particular to the acquisition of multiple, standard sized radiographic images for constructing a larger composite radiographic image using multiple digital radiographic detectors.

BACKGROUND OF THE INVENTION

Full spine and full leg radiographic examinations, useful for assessment of scoliosis and for leg length, angulation, and deformity measurement and other diagnostic functions, require images that exceed the length of normal-sized radiographic films or other types of receiver media. In conventional practice, this extended- or long-length imaging (LLI) problem has been addressed using either of two basic approaches. The first approach uses an extra long, non-standard sized imaging detector. This approach is straightforward and feasible when using x-ray film as the imaging medium, but becomes costly and impractical when using various types of digital radiography media. With Computed Radiography (CR) media, in which a photostimulable phosphor storage sheet or plate is exposed and digitally scanned in separate operations, the dimensions of the storage medium can be constrained by the dimensions of the CR cassette that houses the medium. There may be some flexibility for extending the size of the CR medium, as taught, for example, in U.S. Pat. No. No. 5,130,541 entitled "METHOD OF AND APPARATUS FOR RECORDING AND READING RADIATION IMAGE" to Kawai that shows the use of an elongated CR plate for long-length imaging. However, this approach may prove impractical and the expense difficult to justify for most radiography installations.

For Digital Radiography (DR) detectors that directly transform received exposure energy to digital image data, the problem of extended-length imaging is much more complex and the fabrication and use of an oversized DR detector is seen as prohibitively costly and impractical. Instead, a second approach for extended-length imaging obtains portions of the full image on two or more standard-size detectors, adjusting the translational or angular position of the x-ray source between each image, then uses digital image processing to stitch the obtained sub-images together. This approach is taught, for example, in U.S. Pat. No. 5,111,045, entitled "APPARATUS FOR RECORDING AND READING RADIATION IMAGE INFORMATION" to Konno et al.; in U.S. Pat. No. 5,986,279, entitled "METHOD OF RECORDING AND READING A RADIATION IMAGE OF AN ELONGATE BODY" to Dewaele; and EPO 919856A1, entitled "METHOD AND ASSEMBLY FOR RECORDING A RADIATION IMAGE OF AN ELONGATE BODY" to Dewaele et al. A variation on this approach also sequentially re-positions a single DR detector along the anatomy to be imaged so that the same detector is used to obtain images at two or more positions.

Among the factors that make long-length imaging using a single DR detector more complex is the required image transfer and refresh timing of the DR detector hardware. Even with higher speed circuitry and advanced techniques for image storage and transfer, the time interval required between image captures is on the order of a few seconds. Inadvertent movement of the patient between images can present difficulties for reconstruction of the full length image from individual component images. The timing of DR exposure and detector and radiation source movement or adjustment between images provides significant complications for the designer of DR systems.

Due to the difficulty of this problem, solutions that have been proposed thus far generally require complex interaction and coordination between components that are shifted between positions for obtaining individual images. Translation of the imaging detector relative to the patient has been proposed using various techniques. For example, U.S. Pat. No. 4,613,983 entitled "METHOD FOR PROCESSING X-RAY IMAGES" to Yedid et al. and U.S. Pat. No. 5,123,056 entitled "WHOLE-LEG X-RAY IMAGE PROCESSING AND DISPLAY TECHNIQUES" to Wilson disclose X-ray systems for imaging a human subject lying on a table. Either the table or both the X-ray source and table are then moved to produce, in quick succession, a series of overlapping electronic images which are then combined into an elongated image for display or printing. Similarly, Warp et al. in U.S. Pat. No. 7,177,455 entitled "IMAGE PASTING SYSTEM USING A DIGITAL DETECTOR" teach shifting the position of a DR detector and adjusting the corresponding position of the x-ray source for obtaining individual images that can be stitched together using digital techniques.

As is noted in U.S. Pat. No. 6,944,265 entitled "IMAGE PASTING USING GEOMETRY MEASUREMENT AND A FLAT-PANEL DETECTOR" to Warp et al., a number of techniques have been developed for combining individual images in order to form a composite long-length image. Using various techniques, reference points using identifiable anatomy structures or other features common to two images can be used to properly align them. For most image-stitching routines, an overlap area, with anatomy common to both images is provided along the interface between two adjacent images.

Although techniques disclosed thus far may be workable for obtaining separate images of the patient that can then be stitched together, a number of practical problems remain. One problem of note relates to the amount of time that is required for DR detector response for providing image data following exposure. On-board processing by the DR detector, converting the stored energy for each pixel into equivalent digital data, can take a few seconds. A sizable amount of image data is generated for each image and must be transferred from the DR detector to an external host processor. Even with high-speed data links, it can take 10-15 seconds or longer to transfer the volume of data that is generated. Some improvement in transfer speeds can be anticipated; however, a measurable amount of time will still be required for image transfer and for re-positioning of the detector to the next imaging position. During the interval between images, the patient is likely to move, which complicates the processing task for stitching image data together.

Another problem relates to the relative complexity of conventional solutions for long-length imaging using digital radiography. Using a conventional DR system, for example, the task of moving the gantry-mounted detector and x-ray source to the appropriate positions can require precision re-positioning of a few hundred pounds of supporting hardware during the brief interval between individual images. Thus, in practice, it can be prohibitively difficult to implement some of the proposed long-length imaging solutions for existing DR equipment.

Therefore, it can be appreciated that there is a need for a long-length imaging solution that is streamlined in weight and mechanical complexity, relatively low cost, that reduces the time interval between images, and that reduces the complexity of combining image data at the interface between two different images.

SUMMARY OF THE INVENTION

It is an object of the present invention to advance the art of diagnostic imaging, particularly for long-length x-ray imaging. With this object in mind, the present invention provides an apparatus for obtaining a long length x-ray image of a subject, comprising: a first x-ray detector; a second x-ray detector; an x-ray source having an exposure directing apparatus that is actuable to direct exposure from the x-ray source towards at least a first imaging position during a first interval and a second imaging position during a second interval, with an overlap along a boundary between the at least first and second imaging positions; an x-ray detector holder comprising a detector translation apparatus that is actuable to translate at least one of the first and second x-ray detectors along a length direction to an interim position for one of the first and second intervals and to either the first or the second imaging position for the other of the first and second intervals; and a host controller that is programmed to provide instructions for movement of the x-ray detector holder and exposure directing apparatus.

It is an advantage of the present invention that it provides a system solution for long-length imaging that can be used with different types of detectors in an x-ray system.

These objects are given only by way of illustrative example, and such objects may be exemplary of one or more embodiments of the invention. Other desirable objectives and advantages inherently achieved by the disclosed invention may occur or become apparent to those skilled in the art. The invention is defined by the appended claims.

BRIEF DESCRIPTION OF THE DRAWINGS

The foregoing and other objects, features, and advantages of the invention will be apparent from the following more particular description of the embodiments of the invention, as illustrated in the accompanying drawings. The elements of the drawings are not necessarily to scale relative to each other.

DETAILED DESCRIPTION OF THE INVENTION

Figure 1:
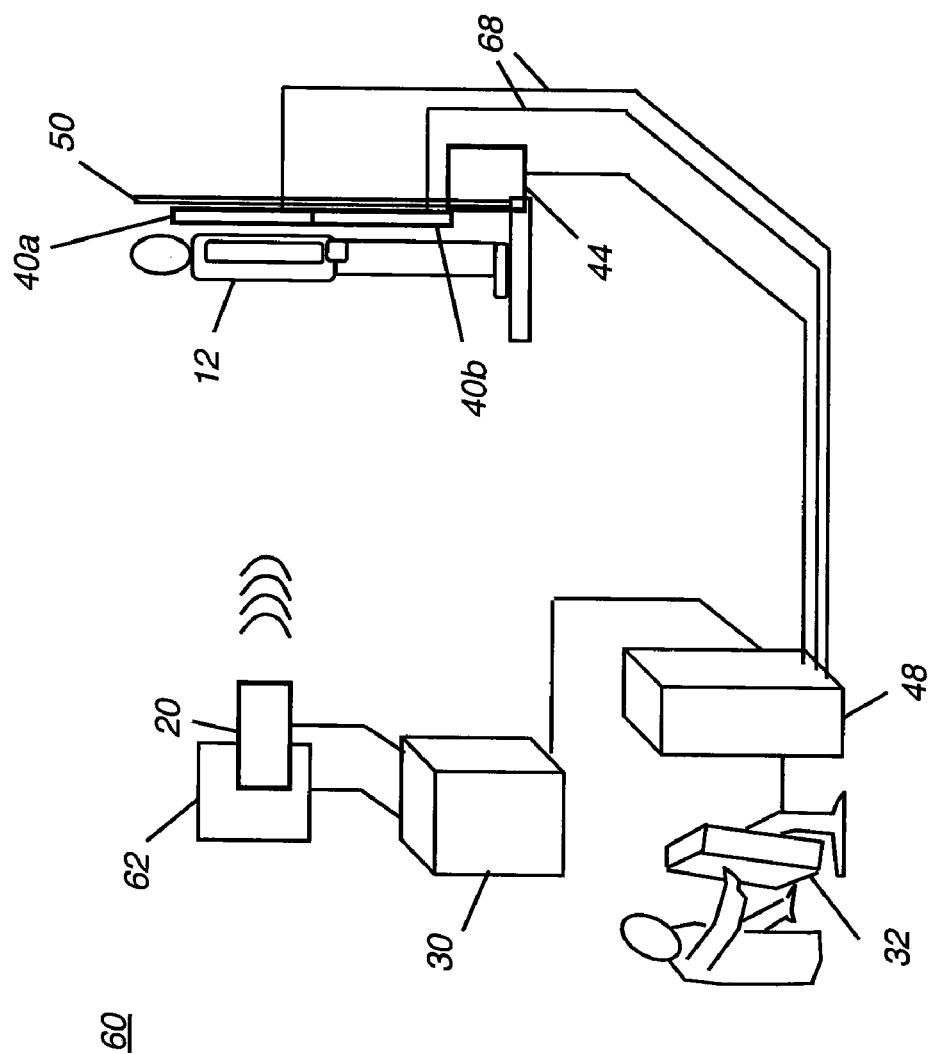
FIG. 1 shows a schematic diagram of an imaging apparatus for providing long-length DR imaging of a patient.

The following is a detailed description of the preferred embodiments of the invention, reference being made to the drawings in which the same reference numerals are used to identify the same elements of structure in each of the several figures. In a number of the figures shown herein, only those components of interest needed for showing general principles of operation are shown. Supporting structures and devices that are used for mounting and supporting the components shown herein are well known to those skilled in the radiographic apparatus arts.

Reference is made to U.S. Ser. No. 12/538,930 entitled "RETROFITABLE LONG LENGTH DIGITAL RADIOGRAPHY IMAGING APPARATUS AND METHOD" filed on Aug. 11, 2009 to Minnigh et al.

Reference is made to U.S. Pat. No. 7,555,100 entitled "LONG LENGTH IMAGING USING DIGITAL RADIOGRAPHY" issued on Jun. 30, 2009 to Wang et al.

Unlike conventional system-based approaches for long-length imaging that repeatedly shift the position of a single x-ray detector in order to obtain each image from that detector, embodiments of the present invention address the problem of long-length imaging by using multiple x-ray detectors and by suitably shifting their positions, relative to the patient, between images. This positional shifting is done in a sequence that achieves a suitable overlap area for subsequent image stitching. This approach helps to reduce the time interval between exposures and thus to reduce problems caused by patient movement during long-length imaging sessions. In addition, embodiments of the present invention require a relatively small amount of movement of the DR detector(s) between imaging positions.

In the context of the present disclosure, the individual images that lie along a length direction and are combined to form a full-length or "composite" image are termed "component images". One consideration for effective long-length imaging relates to the gap at the interface between adjacent image positions. Stitching of adjacent images, as noted in the background section given earlier, requires some overlap between the respective boundaries of adjacent imaging positions.

Referring to FIG. 1, there is shown a schematic diagram of an imaging apparatus 60 for providing long-length DR imaging of a patient 12 using two x-ray detectors 40a and 40b according to an embodiment of the present invention. An x-ray tube 20 provides the needed exposure radiation for imaging, under the control of control circuitry 30 that accepts setup and operation commands from entries made on an operator console 32. The two x-ray detectors 40a and 40b that are used are shown as digital radiography (DR) detectors in FIG. 1, each having a data link 68 to a host processor 48. A detector translation apparatus 44, shown mounted on an x-ray detector holder 50, such as a transport column in the FIG. 1 embodiment, controls the positioning of x-ray detectors 40*a* and 40*b* during imaging. X-ray tube 20 has an exposure directing apparatus 62 that controls the distribution and direction of exposure radiation that is provided. A host processor 48 obtains the digital data from DR detectors 40*a* and 40*b* and provides control signals for detector translation apparatus 44.

The basic arrangement of FIG. 1 allows a number of alternative embodiments. For the DR detector example shown, data link 68 can be wired, as shown in FIG. 1, or wireless, such as using RF, infrared, or other signal transmission mechanism for downloading the image data from each of DR x-ray detectors 40*a* and 40*b*. Alternatively, other types of x-ray detector can be used, including those not using data link 68, such as a computed radiography (CR) detector that is positioned and exposed in the same manner but must be removed following exposure and scanned in a separate operation in order to obtain its stored data. A film cassette could alternately be used. Hybrid arrangements that use combinations with one or more DR detectors, CR detectors, or film cassettes could alternately be used. DR detectors are advantaged because they do not need to be removed for processing and can be refreshed prior to obtaining an image, so that scattered radiation from an earlier exposure is erased prior to imaging. Film or CR detectors would require some type of shielding when not in use in order to reduce the effect of scattered radiation. Exposure directing apparatus 62 can be any of a number of types of devices, such as those that use a combination of a collimator with a directional mask aperture or similar device. In one embodiment, exposure directing apparatus 62 uses a tilt mechanism for orienting the angle of the radiation energy for each exposure.

Figure 2:
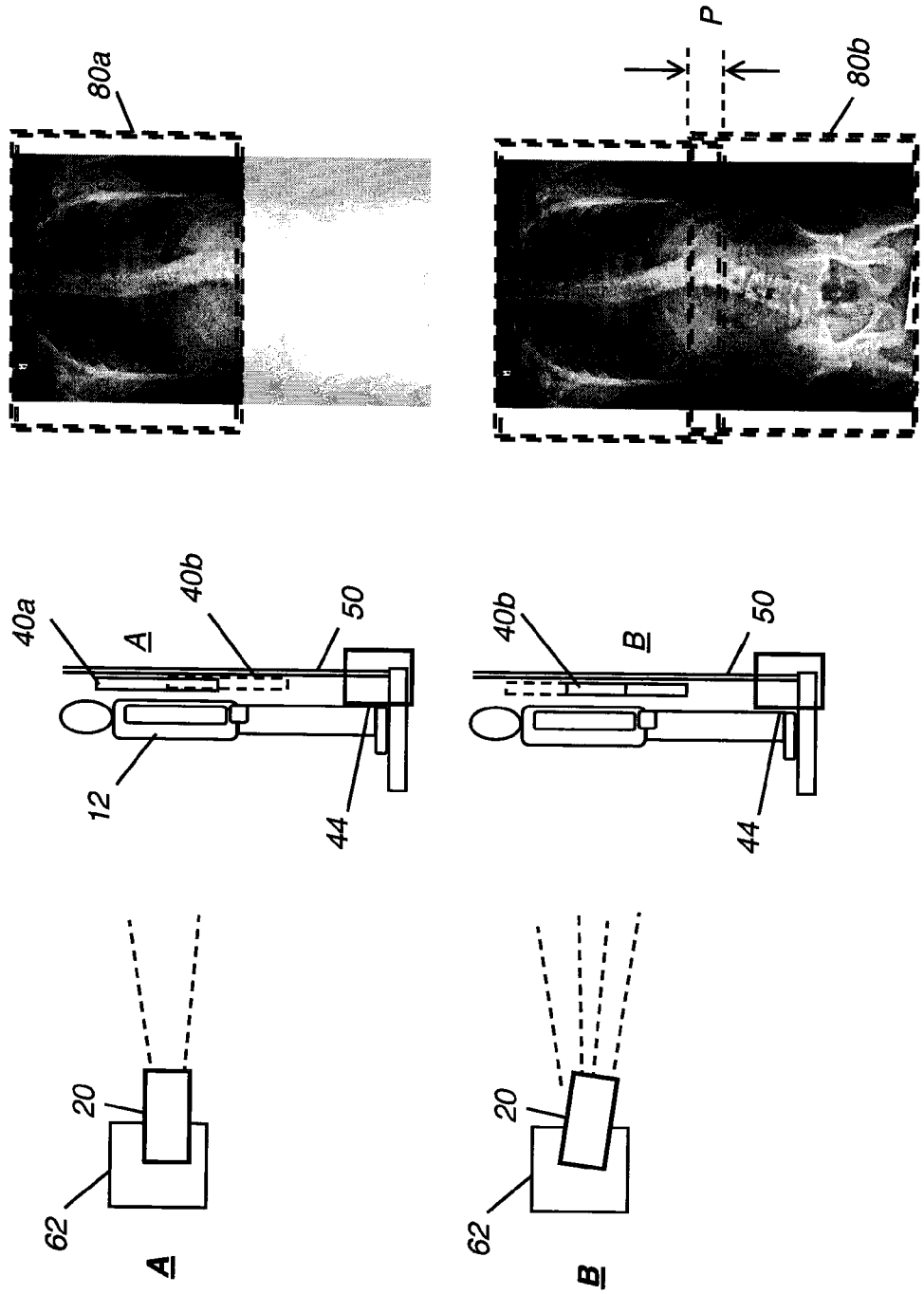
FIG. 2 shows a schematic diagram with images obtained at two positions.

The diagram of FIG. 2 shows the basic positioning that is required for long-length imaging when using two x-ray detectors 40*a* and 40*b*. The figure also shows how each portion of a longer image is obtained. Representative images are shown at the right in this figure. At imaging position A, exposure directing apparatus 62 directs the radiation from x-ray source 20 to DR detector 40*a* at an upper position, such as for chest imaging. An upper position image 80*a* is obtained. Once upper position image 80*a* is obtained, exposure directing apparatus 62 then redirects radiation from x-ray source 20 to DR detector 40*b* at a lower position along the length direction, as shown in imaging position B. At imaging position B, exposure directing apparatus 62 directs the radiation from x-ray source 20 to DR detector 40*b* to obtain image 80*b*. There is a slight overlap P, along the edge or boundary between imaging positions A and B, that is used for correlating image content so that adjacent images can be properly "stitched together" to form a single long-length composite image from two adjacent, component images. Detector translation apparatus 44 can operate in a number of ways to translate the appropriate detector into each position for imaging. For example, detector translation apparatus 44 can be servo-driven, using one or more rollers, belts, or other mechanisms for positioning detectors 40*a* and 40*b*. Alternately, detector translation apparatus 44 can use gravity to shift detector position, including mechanisms that employ dampened gravity, for example.

Exposure directing apparatus 62 can be any of a number of devices for directing the x-ray radiation from x-ray source 20 toward an appropriate detector. In embodiments shown herein, tilt mechanisms are provided for directing the radiation to an appropriate detector. An optional collimator or movable aperture may be used as an alternative to, or in addition to, a tilt mechanism for directing exposure energy. Another alternative is a translation mechanism that translates the spatial position of x-ray source 20 in a linear direction for exposing a subject at successive imaging positions.

Figure 3A:
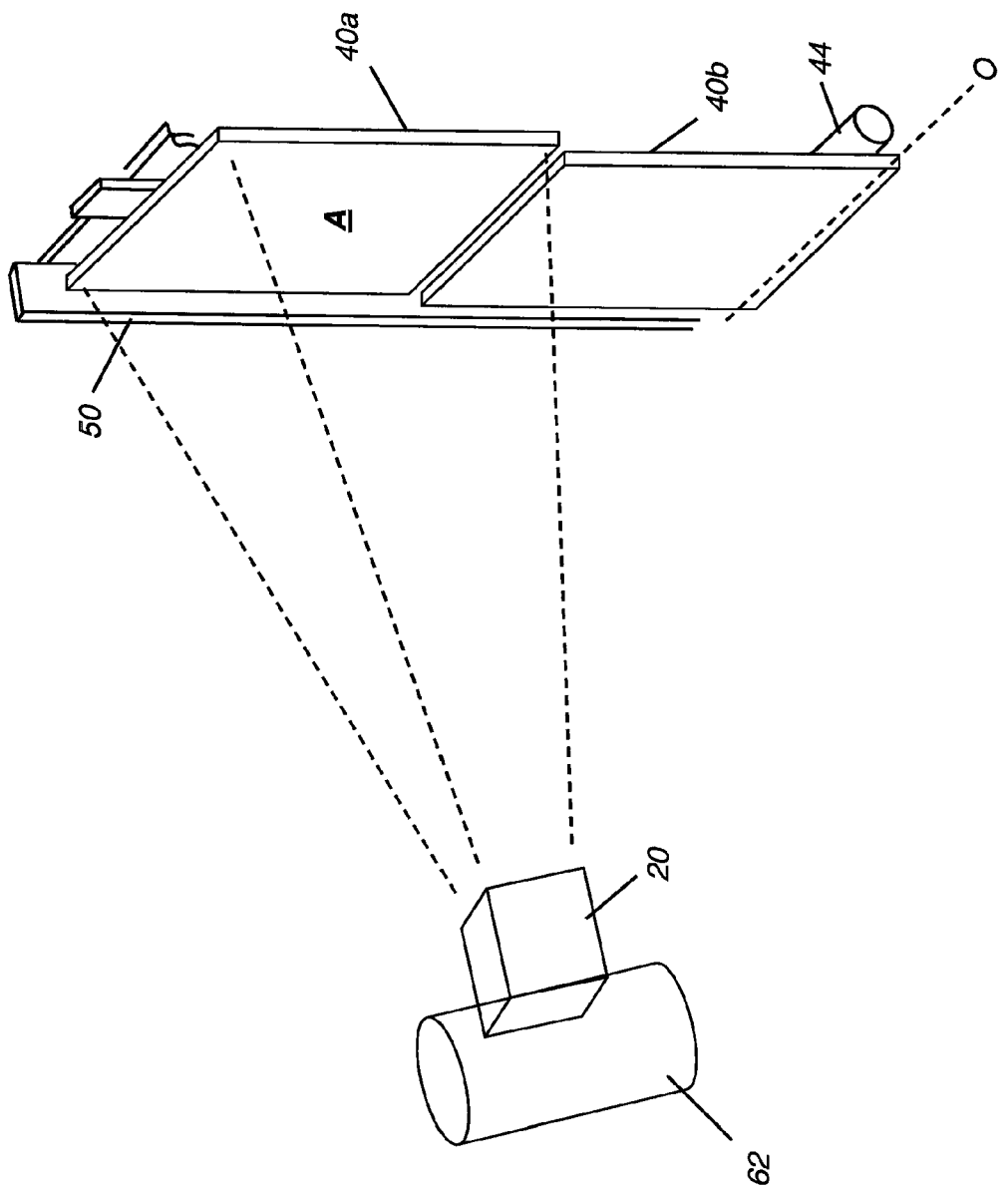
FIGS. 3A and 3B are perspective views that show how detector translation apparatus and exposure directing apparatus cooperate to provide long-length imaging in one embodiment.
Figure 3B:
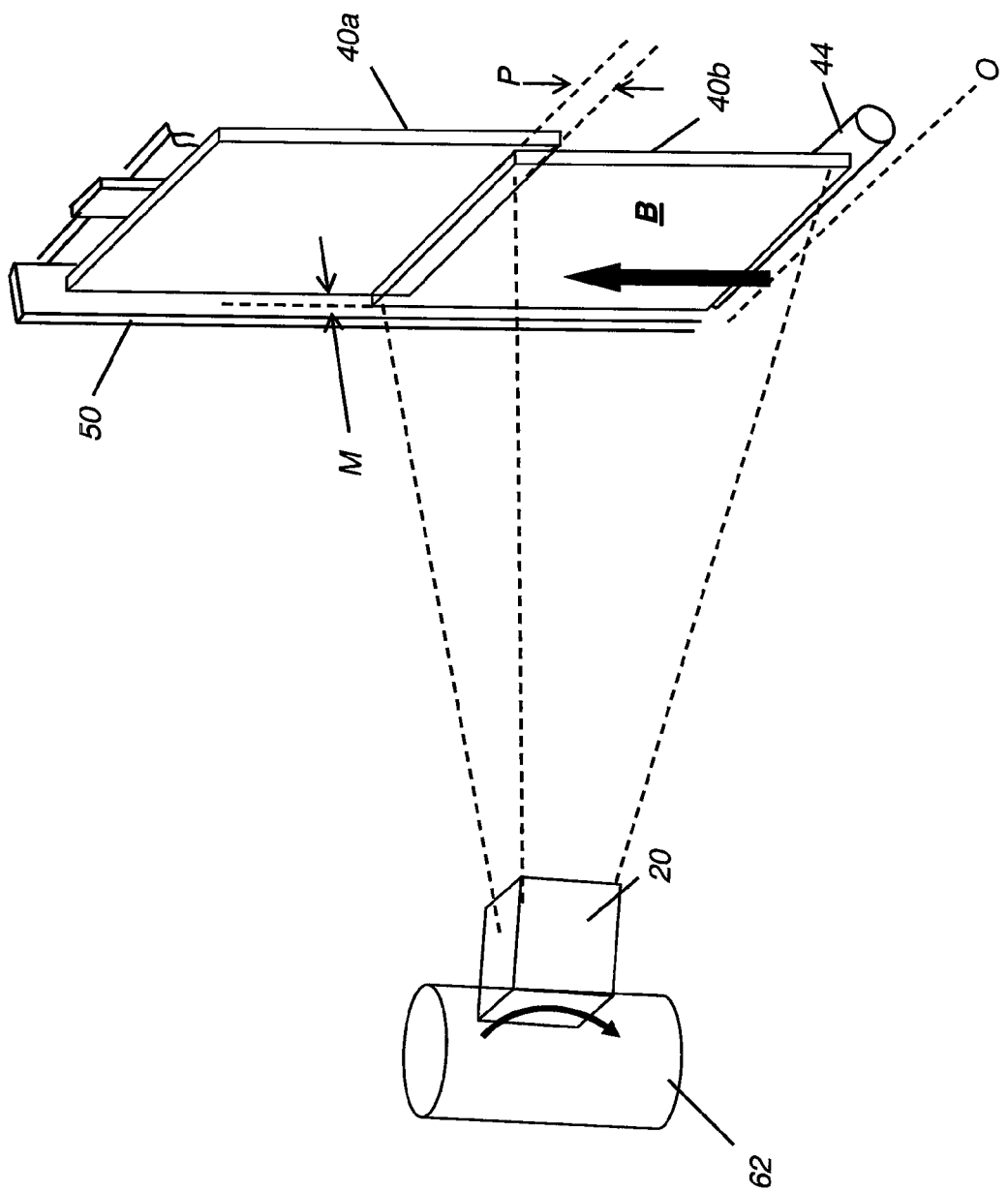

The perspective views of FIGS. 3A and 3B show how detector translation apparatus 44 and exposure directing apparatus 62 cooperate to provide long-length imaging in one embodiment. Here, x-ray detector 40*a* is fixed in position and x-ray detector 40*b* movable, as controlled by detector translation apparatus 44. FIG. 3A shows the relative position of these components for exposure of upper x-ray detector 40*a*. Initially, during the first exposure interval, lower x-ray detector 40*b* is in an interim, that is, non-imaged, position, with its base aligned vertically at original position O. Following this first exposure interval, as shown in FIG. 3B, exposure directing apparatus 62 re-orients the radiation energy for exposure of lower x-ray detector 40*b*. Prior to this second exposure interval, lower x-ray detector 40*b* is moved upwards from original interim position O so that it overlaps a bottom portion of the edge of upper x-ray detector 40*a* by an exposure overlap P. Typically, overlap P is on the order of about 4 cm in one embodiment. Arrows in FIG. 3B indicate directions of movement from positions of FIG. 3A. In this embodiment, x-ray detectors 40*a* and 40*b* are not in the same plane, but have a slightly different source-to-image distance (SID) that may be acceptable in some imaging applications or can be corrected by image interpolation resizing. In one embodiment, the magnification factor between images taken from detectors 40*a* and 40*b* is adjusted to compensate for the slight offset distance M shown in FIG. 3B.

Figure 3C:
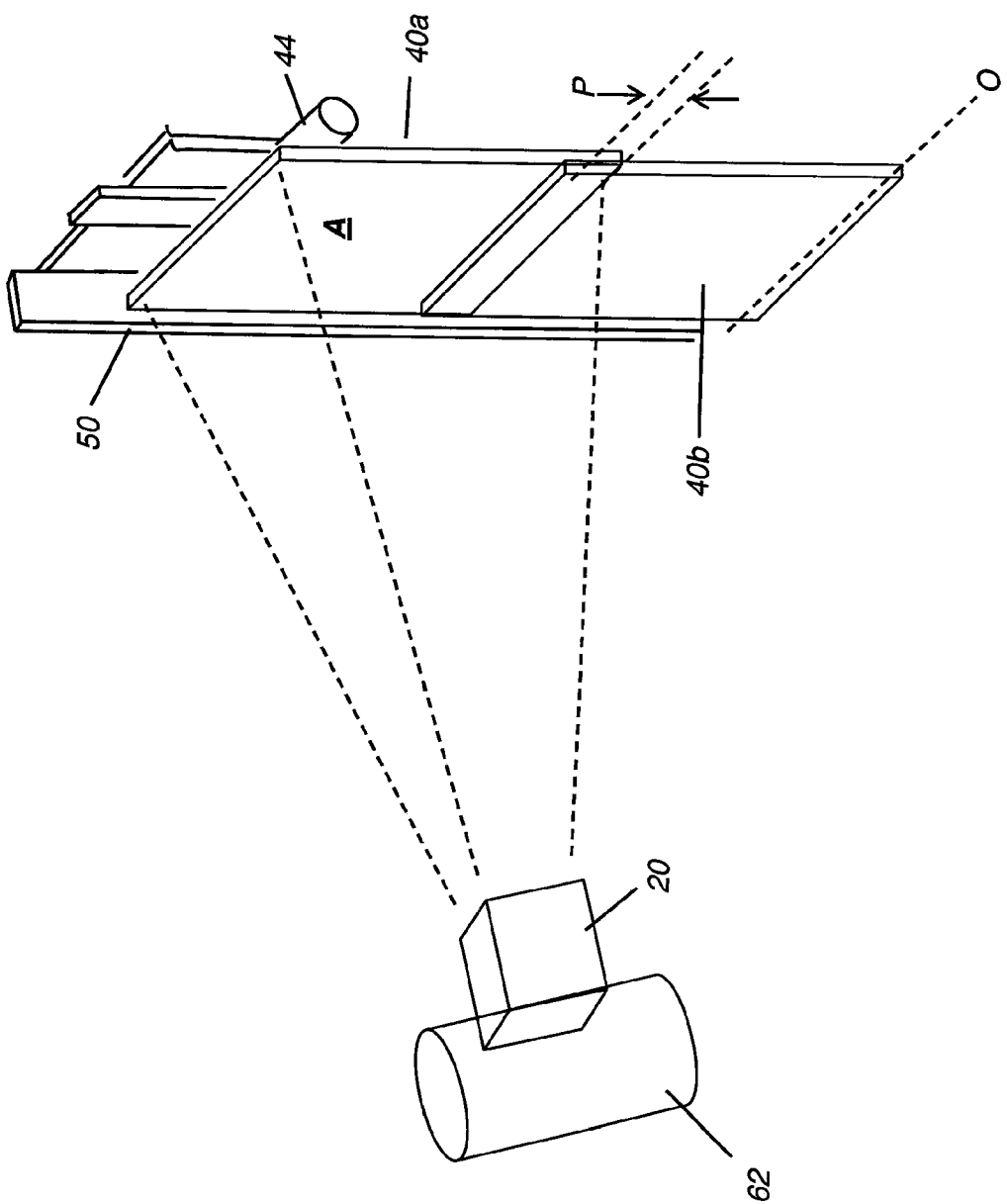
FIGS. 3C and 3D are perspective views that show how detector translation apparatus and exposure directing apparatus cooperate to provide long-length imaging in an alternate embodiment.
Figure 3D:
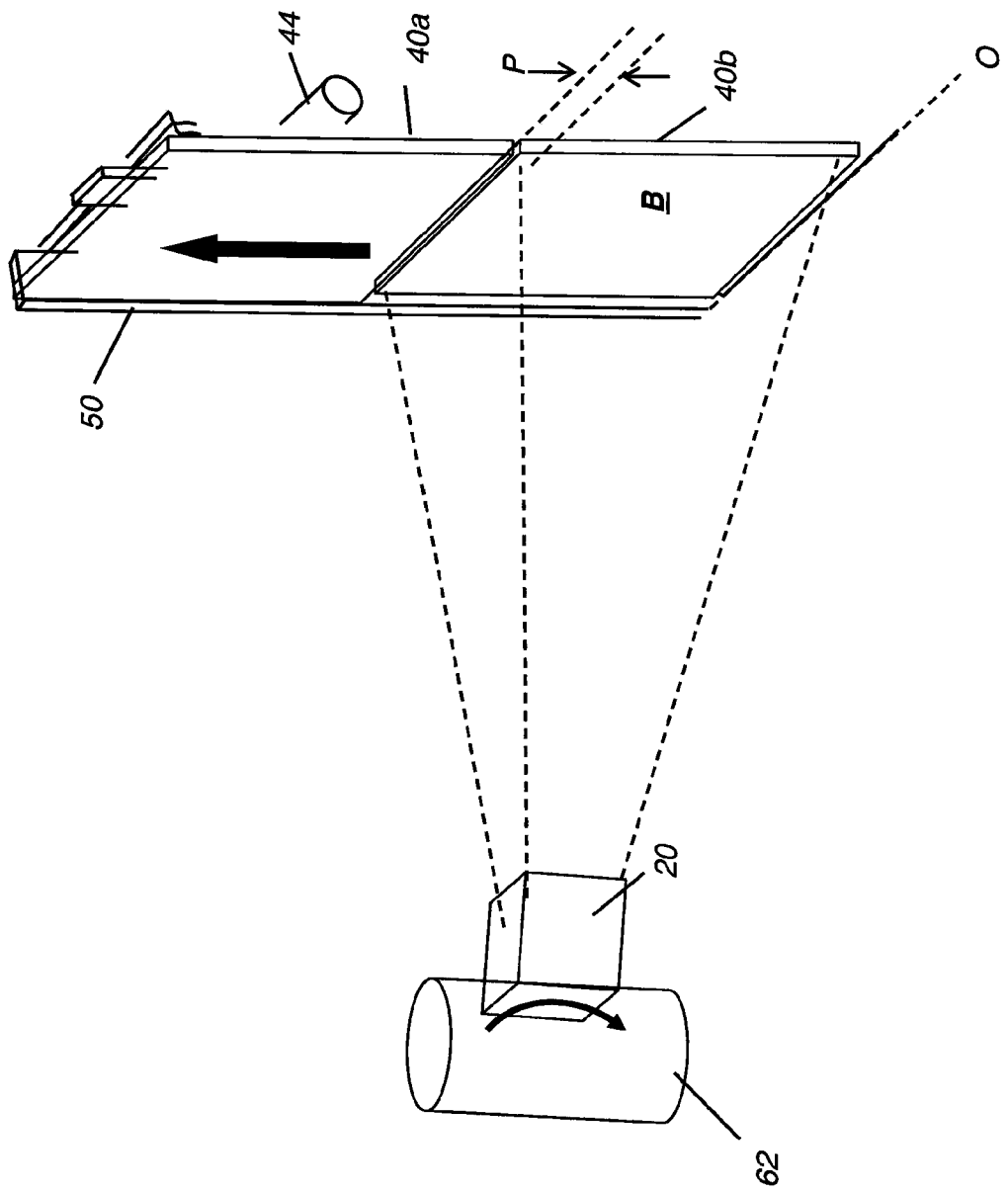

The perspective views of FIGS. 3C and 3D show how detector translation apparatus 44 and exposure directing apparatus 62 cooperate to provide a sequence of images for long-length imaging in an alternate embodiment. Here, for the first exposure interval, movable x-ray detector 40*a* overlaps the top edge of x-ray detector 40*b* to expose the first image at a first imaging position with the arrangement shown in FIG. 3C. Then, to obtain the second image in the series, as shown in FIG. 3D, x-ray detector 40*a* is raised to an interim position prior to the second exposure interval and exposure directing apparatus 62 re-orients the radiation energy for exposure of lower x-ray detector 40*b*, which remains stationary.

Figure 4A:
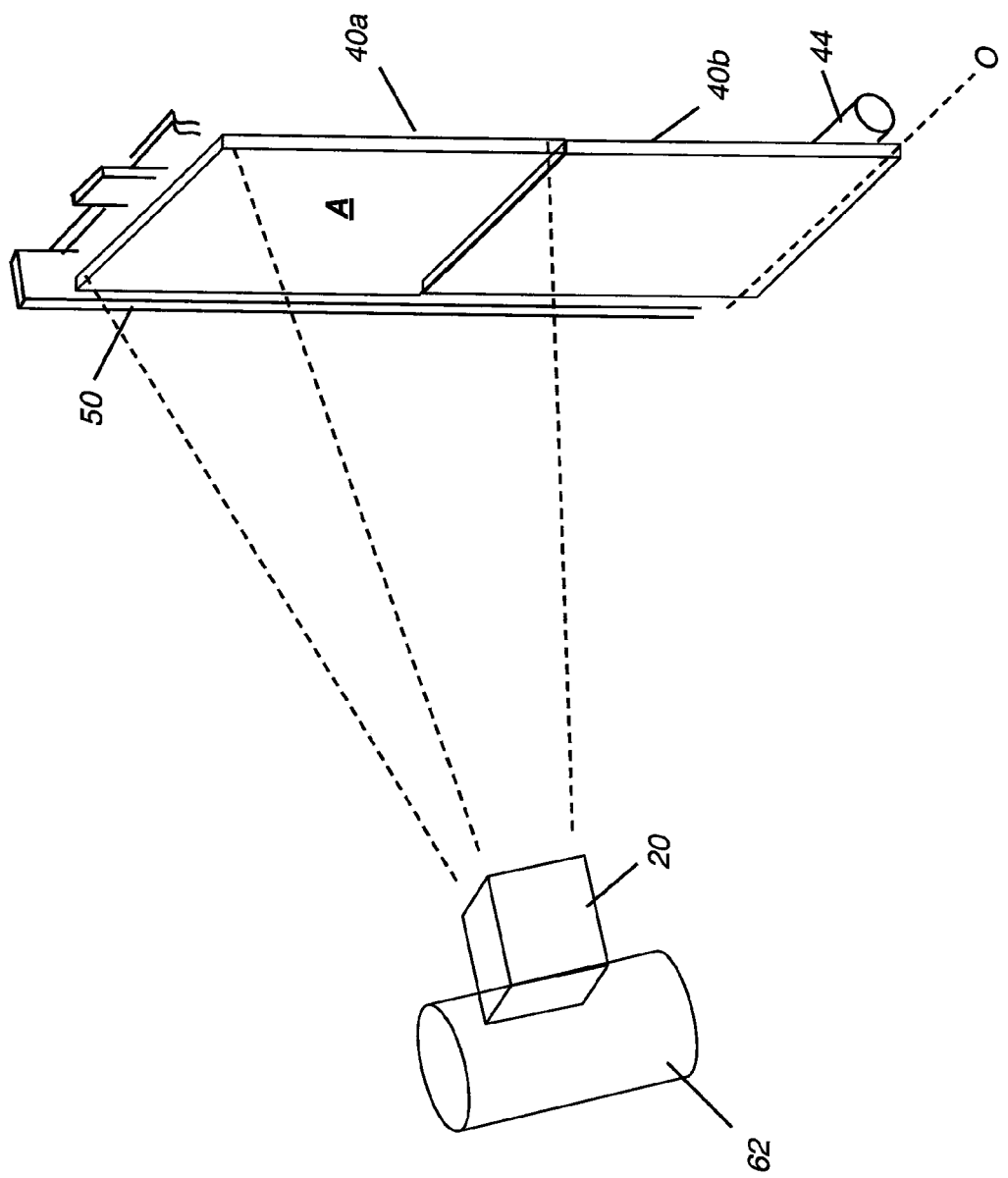
FIGS. 4A and 4B are perspective views that show how detector translation apparatus and exposure directing apparatus cooperate to provide long-length imaging in another alternate embodiment.
Figure 4B:
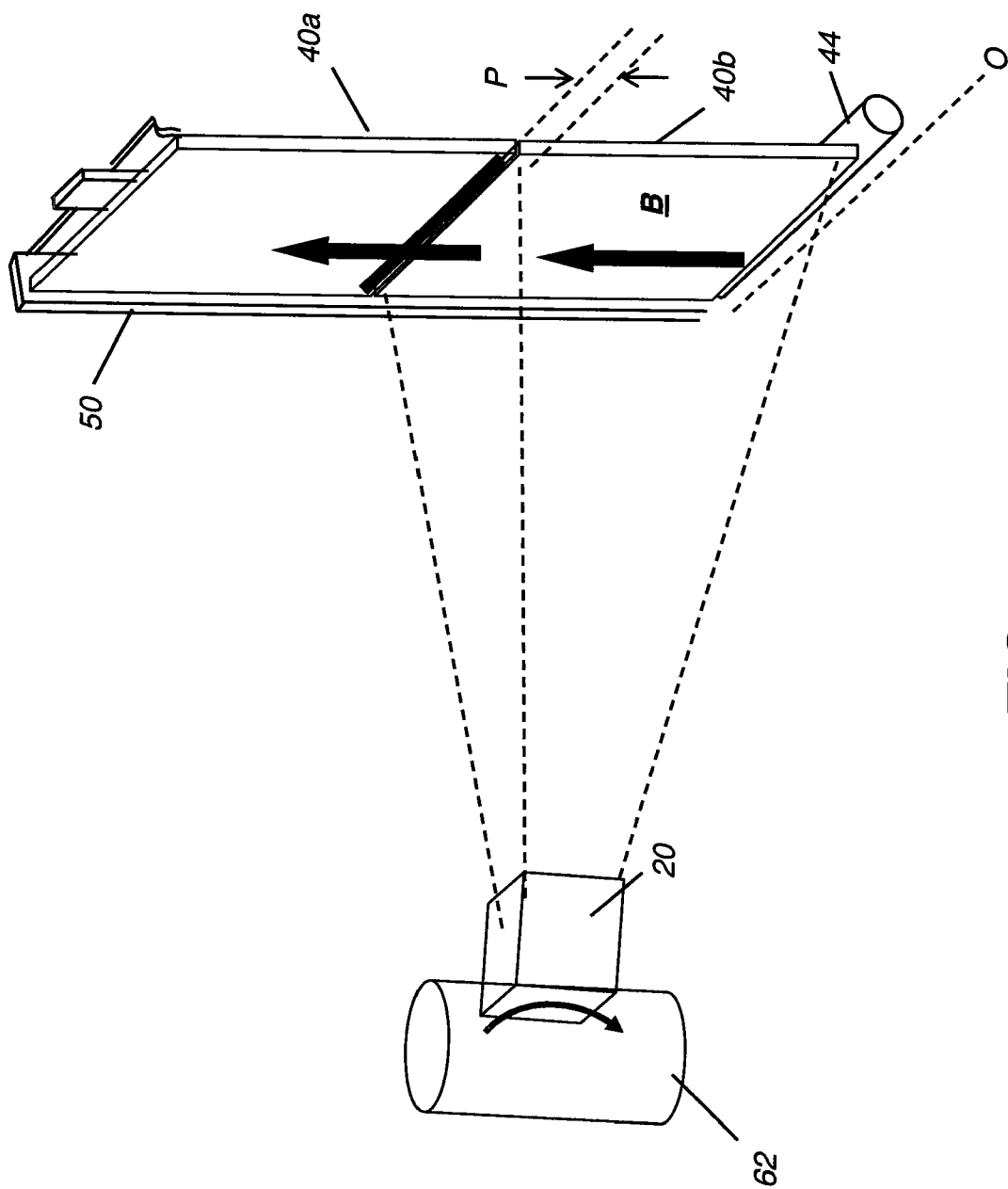

The perspective views of FIGS. 4A and 4B show how detector translation apparatus 44 and exposure directing apparatus 62 cooperate to provide long-length imaging in another alternate embodiment. Here, x-ray detectors 40*a* and 40*b* are in the same plane. In the embodiment of FIGS. 4A and 4B, x-ray detectors 40*a* and 40*b* are aligned in the same vertical plane and travel together, as controlled by detector translation apparatus 44. FIG. 4A shows the relative position of these components for exposure of upper x-ray detector 40*a* in a first imaging position. Initially, when detector 40*a* is exposed over the first exposure interval, the bottom of lower x-ray detector 40*b* is vertically aligned at original non-imaging interim position O. Then, following this first exposure, exposure directing apparatus 62 re-orients the radiation energy for exposure of lower x-ray detector 40*b* to second imaging position B during the second exposure interval, as shown in FIG. 4B. Prior to this second exposure interval, both x-ray detectors 40*a* and 40*b* are translated upwards from original interim position O, by the exposure overlap P, so that the second imaging position B overlaps the position of a bottom portion of upper x-ray detector 40*a* when in the first imaging position A by an exposure overlap P. Arrows in FIG. 4B indicate directions of movement from the original positions of FIG. 4A.

Figure 5:
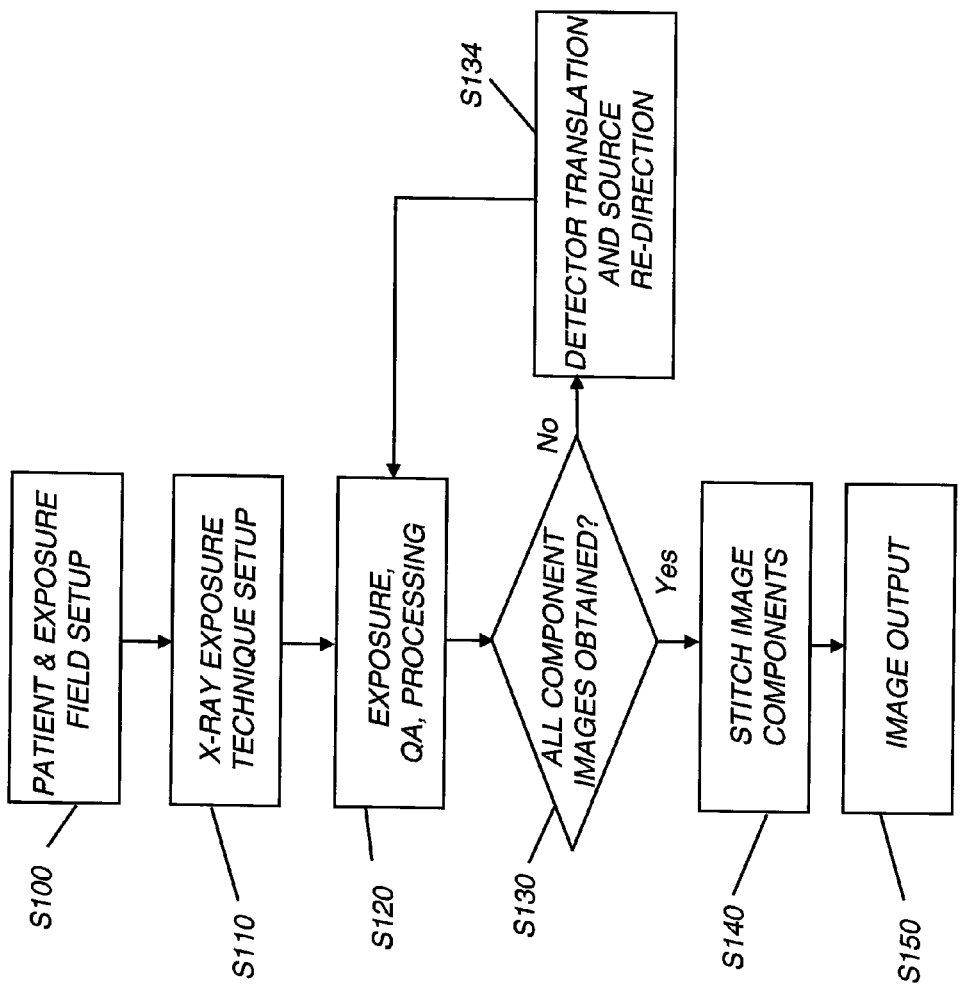
FIG. 5 is a logic flow diagram showing a sequence for obtaining a long-length image using the apparatus of the present invention.

The logic flow diagram of FIG. 5 shows steps for long-length imaging using the apparatus and method disclosed herein. In a setup step S100, the technologist positions the patient as needed for the requirements of the exam.

This may mean positioning in the upright or supine position, for example. Then, using system controls or manual positioning, or some combination of the two, the technologist sets up the exposure field for long-length imaging. In one embodiment, the technologist simply sets an initial imaging position and then sets up one or more additional imaging positions according to factors such as the length of the area being imaged, the amount of overlap that is used between images, the positions of overlap areas relative to patient anatomy, the dimensions of the DR detector itself, and other factors. This setup thus determines the number of images that must be obtained and their relative positions. Additional details on setup factors and considerations for long-length imaging are given subsequently.

The technologist has a number of tools available from imaging apparatus 60 for facilitating long-length imaging setup. For example, for setting up the initial positions of x-ray source 20 and the initial height of DR detector 40, the technologist typically uses the visible light aiming tool that is available with the x-ray tube collimator aperture, thereby identifying the desired anatomical region of the patient. The visible light from the collimator, representative of the full, actual x-ray exposure coverage, assists in determining the total exposure area on the patient in similar manner to that used for a screen film system. The system for one embodiment uses the area marked by visible light as the system controlled exposure area as well.

Note that, in setup step S100 of FIG. 5, the collimator size may exceed the dimensions of the full sized exposure field defined by the x-ray detector dimensions. Positional and component distance feedback, including information about collimator size, can be provided to host processor 48 control logic for the imaging system (FIG. 1). This allows computation of the number of exposures needed in an exposure series and computation of the actual exposure size, as is described subsequently. In this way, a long length imaging mode of system operation is obtained using setup step S100. Additional manual procedures may also be required, such as manually setting exposure directing apparatus 62 or manually specifying x-ray detector 40a, 40b locations, for example.

Continuing with the sequence of FIG. 5, an x-ray exposure technique setup step S110 follows, in which the technologist determines and sets up the overall x-ray technique parameters that provide instructions for imaging, as described in more detail subsequently. Then, to begin an exposure and processing step S120, the technologist initiates the full exposure series by a command entry, such by pressing an exposure button on operator control console 32, for example. After the exposure is captured, a decision step S130 then determines whether or not one or more additional exposures are still needed to complete the series. If so, a translation step S134 is then executed, in which both detector and x-ray source hardware are translated to the next imaging position, in preparation for another iteration of step S120 and another exposure interval. If all images have been captured, an image stitching step S140 is executed and an image output step S150 provides the final, assembled long-length image.

It is noted that the basic sequence shown in FIG. 5 allows a number of variations in different embodiments of the present invention. For example, Quality Assurance (QA) information may be generated and assessed at any of a number of different points as images are captured. The basic sequence of FIG. 5 can operate in a fully automated mode, for which a single command entry or button press initiates the full sequence for obtaining and stitching together two or more images. An interrupt is provided to give the operator the capability to stop this continuous sequence. In a prompting mode, the technologist may be prompted for detecting each component image following translation step S134, for example. Either mode would thus allow the technologist to stop the imaging process, such as due to patient condition, excessive movement, safety, or other concern.

To facilitate image stitching in one embodiment, encoders or other suitable types of sensors are used to control and detect position and operation of various mechanical components of the system and their operating parameters, including, but not limited to, the detector position, tube position, mask or aperture position, tube rotation angle, collimator aperture size, and collimator shutter position.

Setup Step S100 Parameters

Figure 6:
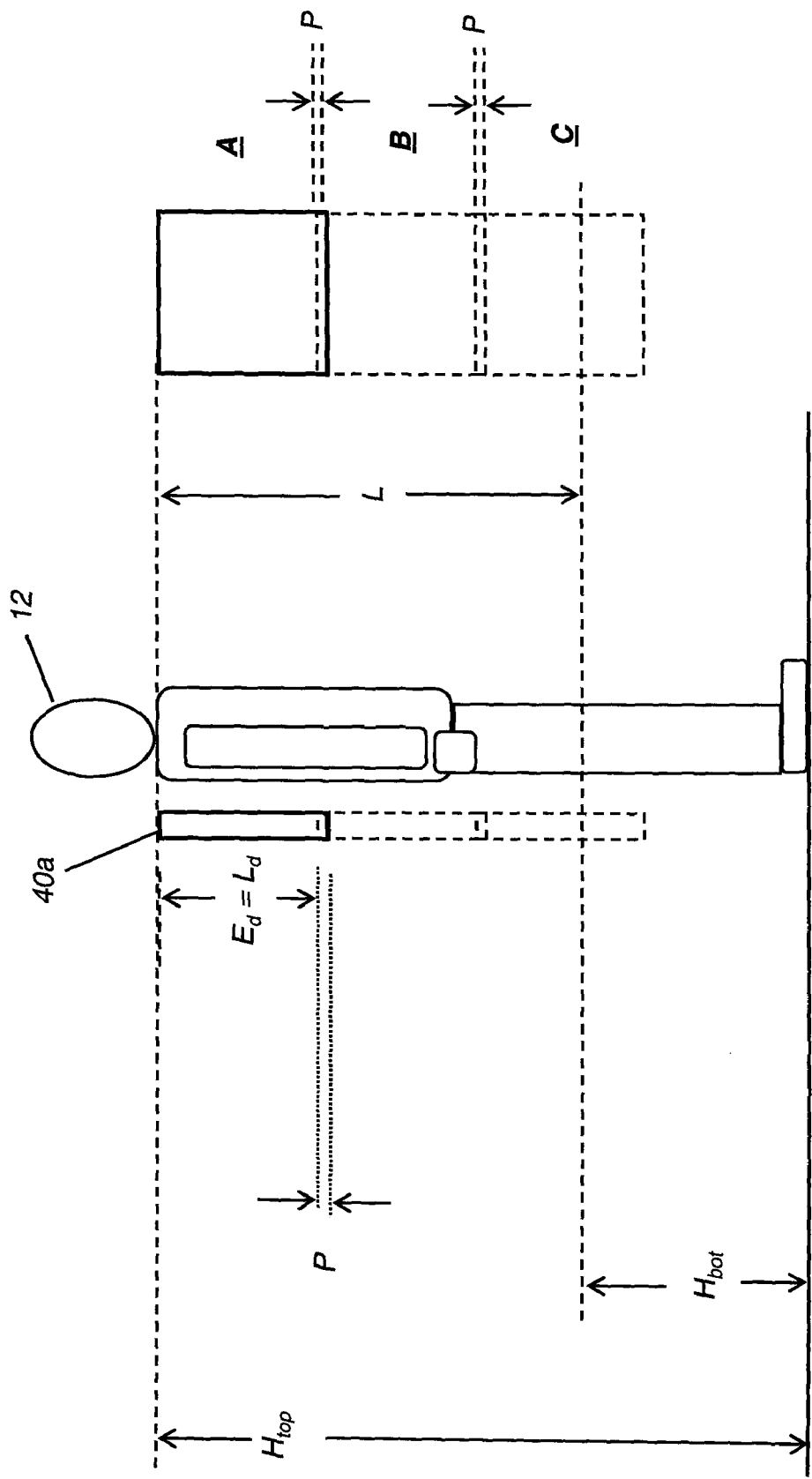
FIG. 6 is a schematic diagram showing detector positioning for multiple images.
Figure 7:
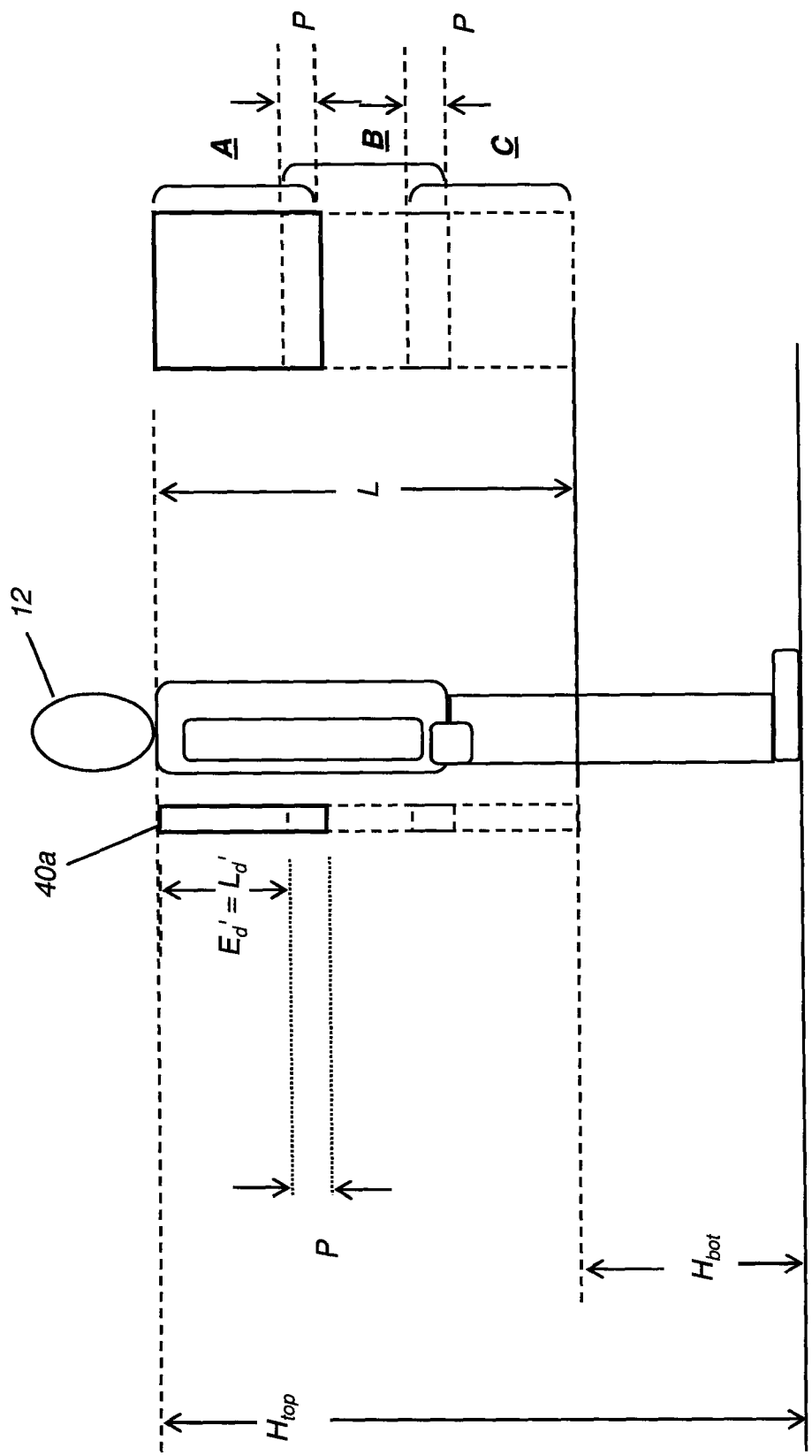
FIG. 7 is a schematic diagram showing detector positioning for multiple images with images of the same dimension.

Setup step S100 determines the number of images n that must be obtained for a particular patient and identifies the required positions of x-ray detectors and exposure for providing each of these images. FIGS. 6 and 7 show examples in which three images, one taken at each of positions A, B, and C, are obtained for stitching together in one embodiment. For these examples, a number of variables are defined, as follows:

L is the overall exposure length that is needed;

$L_d$ or $L_d'$ gives the effective exposure length on the x-ray detector, available for each single image;

$E_d$ or $E_d'$ gives the exposure field size, as computed, set equal to the corresponding effective exposure length $L_d$ or $L_d'$;

P is the minimum exposure overlap that is required along boundary edges between adjacent image positions for stitching.

In the example shown in FIG. 6, the number of exposures N that are taken along the length direction can be computed as follows:

$$N=(int)[(L-P)/(L_d-P)+1]$$

wherein the (int) operator takes the integer part of the result given in brackets [ ].

In step S100 (FIG. 5), the x-ray technologist initially establishes the height of the image area, thus the exposure length L by specifying at least two variables that define boundaries:

$H_{top}$ Floor or other reference to top of radiation field;

$H_{bot}$ Floor or other reference to bottom of radiation field.

In embodiments where a mask or aperture is used for redirection of radiation, x-ray source 20 can remain stationary between exposures. Its radiation field is then set up initially to extend over the full image height. In practice, this can be accomplished by adjusting a collimator so that the visible collimator light illuminates the full field desired for imaging, without consideration of x-ray detector height. Sensors on the collimator itself can report the size of the collimator opening to system logic, or this dimension can be measured in some other way. This data can then be used in combination with other information on source-to-image distance (SID) in order to determine the full extent of the image area, with length corresponding to exposure length L as shown in FIGS. 6 and 7.

Knowing length L, overlap P, and effective exposure length parameter $L_d$, the number of exposures that are needed can be readily computed. For the embodiment of FIG. 6, three exposures are needed. One exposure in the series that is obtained has an exposure field that uses only a smaller portion of the available detector area. Alternately, in the embodiment shown in FIG. 7, substantially equal portions of a detector of dimension $E_d'=L_d'$ are used for each of the three exposures, with the overlap value P also changed accordingly. Parameter $H_{top}$, or alternately $H_{bot}$, along with length L, serves to locate the starting-point or ending point of a series of overlapped images for long-length imaging.

The calculations that are needed for positioning an x-ray detector and source for long-length imaging are not complex and are well within the scope of capabilities of an experienced technologist. The following general observations are particularly pertinent to the long-length imaging environment of embodiments of the present invention:

(i) The series of two of more images that are obtained can be taken in any order. In general, top-to-bottom, bottom-to-top, left-to-right, and similar sequencing based on adjacent position is more practical; however, there can be situations in which it is advantageous to change the positional ordering.

(ii) Collimator and aperture settings can be adjusted to accommodate for images that have an exposure field that is smaller than $L_d$, as in the example of FIG. 7.

(iii) Mask aperture settings may or may not be adjustable between exposures, depending upon the equipment configuration.

(iv) In general, it is advantageous to use a sequence that minimizes the time between exposures. This reduces the likelihood of patient movement that can complicate registration and image stitching in step S140 (FIG. 5).

(v) Exposure lengths for each image in a series can vary from each other. It may be advantageous, for example, to adjust the placement of overlap P relative to patient anatomy, such as to reduce exposure energy to the heart or other more sensitive tissues or to position the overlap area for easier image stitching.

For the FIG. 6 example, where N exposures are taken in sequence from top to bottom, the effective exposure field size $E_n$ on the detector is the same, $L_d$, for the first N-1 exposures, but is smaller for the last exposure, $E_N$ at position C.

$$E_n = L_d \text{ when } n=1, 2, \ldots N-1$$

and $$E_N = L - [(N-1)L_d - (N-2)P]$$

The FIG. 7 embodiment is an alternate arrangement in which all of the exposure field sizes for imaging positions A, B, and C are equal, the vertical travel distance for the detector is the same to reach each exposure position, and the dimensional settings for the x-ray source are the same for each imaging exposure position. For FIG. 7, the following are computed as was described with reference to the example of FIG. 6: a number of exposures required, a top $H_{top}$ and a bottom $H_{bot}$ of the radiation field, an overall exposure length L, and a minimum exposure overlap P required for stitching. The exposure field size $E_n$ are of equal size for imaging positions A, B, and C, and are obtained by setting an effective exposure field size $L_d'$ to:

$$L_d' = (L-P)/N + P.$$

In this method, an effective exposure field size $E_n$ (n=1, 2 ... N) will be the same, for all the exposures.

$$E_n' = L_d'$$

The calculation of detector stop positions $H_n$ (for n=1, 2, ..., N) is obtained using:

$$H_n = H_{bot} + L_d'/2 + n \times (L_d' - P).$$

Various levels of automation or technologist interaction can be employed for setting up the sequence of exposures. In one embodiment, manual setup is used for detector and x-ray source positioning for multiple exposures. Prior to imaging, the technologist interacts with controller hardware to set up and store the needed detector and source positions, using the visible light aiming tool that is available with the x-ray tube collimator, for example, to manually establish each imaging position. A logic command entered by the technologist then instructs the respective controller circuitry (FIG. 1) to remember each position in the sequence.

Figure 8:
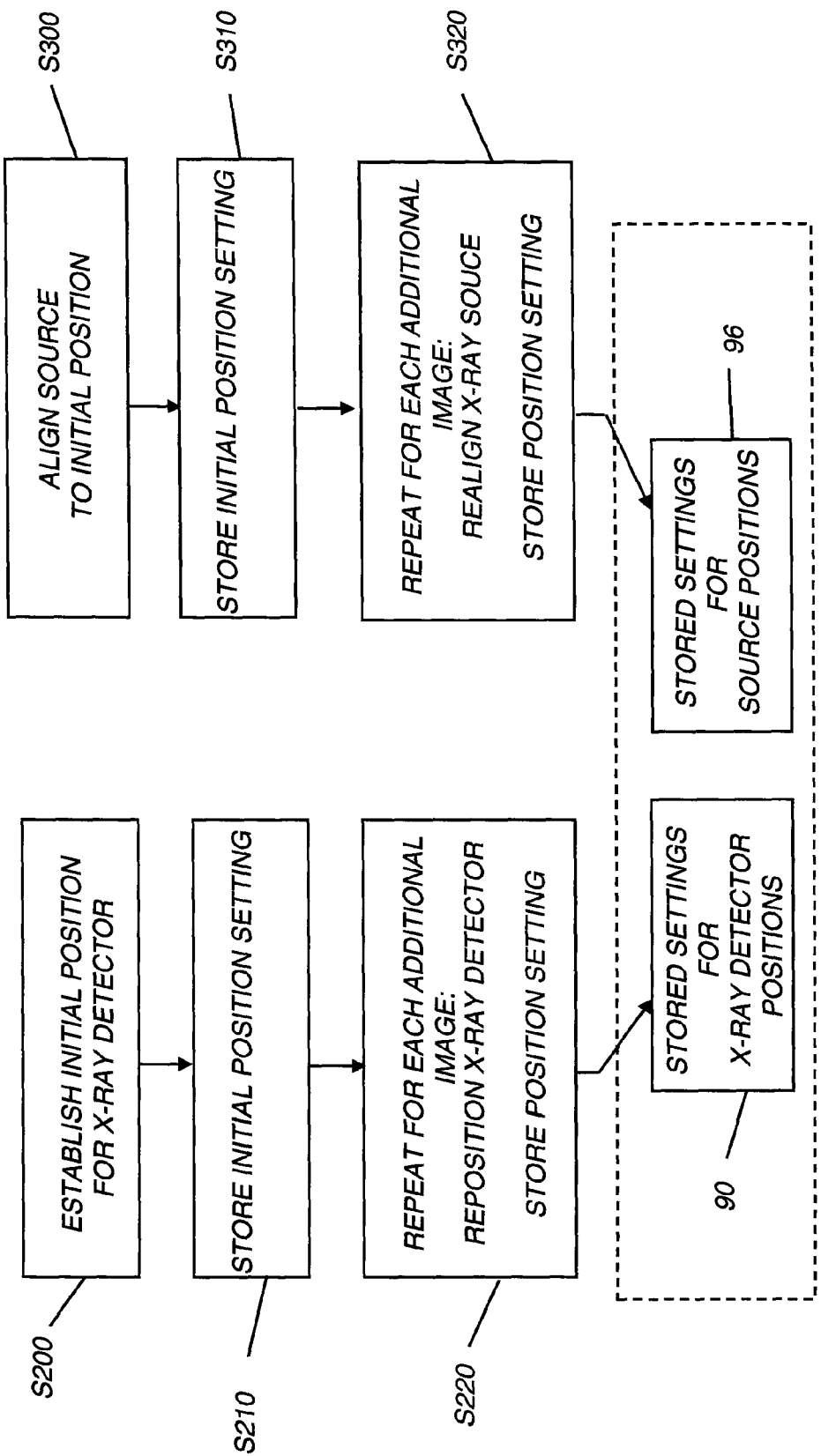
FIG. 8 is a logic flow diagram showing setup steps for storing position data for the mask and the detector in one embodiment.

The logic flow diagram of FIG. 8 shows the setup steps for obtaining the respective positions of the DR detector and exposure in one embodiment using manual positioning by the technologist. For this embodiment, an interactive session is used to store position data so that it is accessible to detector translation apparatus 44 (FIG. 1). Interaction with the technologist can be performed using command entries at detector translation apparatus 44 or using the operator interface to host processor 48, for example.

For x-ray detector positioning, shown in the left column of steps in FIG. 8, an initial setup step S200 obtains the first position for the detector. In a storage step S210, this initial position information is stored in a memory that is accessible to detector translation apparatus 44. A looping step S220 then has the technologist repeatedly repositioning the x-ray detector and storing the settings for each of the subsequent detector positions. At then end of this process, stored settings 90 are then available for positioning the x-ray detector at each imaging position.

X-ray source 20 positioning, shown in the right column of steps in FIG. 8, is executed in similar fashion, coordinated by the technologist with the steps for DR detector positioning just described. An initial setup step S300 obtains the first position for the source. In a storage step S310, this initial position information is stored in a memory on host processor 48. A looping step S320 then has the technologist repeatedly repositioning the source along the length direction and storing the settings for each of the subsequent positions. At then end of this process, stored settings 96 are then available for positioning the x-ray source to expose each imaging position. Stored settings 90 and 96 are stored in the same storage component or memory in one embodiment, then used by host processor 48 to control and coordinate the positioning of long-length imaging components for imaging apparatus 60.

Using a sequence similar to that shown in the embodiment of FIG. 8, data for positioning the detector and the x-ray source are obtained and stored for stepping through the long-length imaging sequence. In an alternate embodiment, the technologist may simply provide starting and ending coordinates for long-length imaging to the control logic on host processor 48. Automated tools are then used for automatically obtaining suitable positions for the detector and x-ray source in the length direction along the long-length imaging path, including calculating overlap and calculating the amount of translation between exposures and related values, as described earlier with reference to FIGS. 3A-7. Stored algorithms then compute appropriate positions and sequencing for detector and source positions or angles. Other arrangements using varying amounts of technologist interaction and automated control and logic may be provided. It should be noted that even where automated tools are used, technologist review of machine-generated placement coordinate information and other factors is generally recommended. For example, it may be beneficial for the technician to make adjustments, such as an adjustment that shifts an overlap position to reduce exposure that is delivered to particular anatomy.

Exposure Technique Setup Step S110

At the completion of setup step S100 (FIG. 5), the variable dimensional factors have been determined and any other mechanical setup needed for long-length imaging execution have been carried out. In the subsequent exposure technique setup step S110, a number of technique variables are determined by the technologist, including but not limited to kVp, mAs, automatic exposure control (AEC) usage, exposure compensation factor (ECF), beam filtration, and anti-scatter grid settings, for example. In film screen radiography for full-spine and full-leg exams, a specially built beam intensity compensation filter is commonly used to pre-attenuate the beam intensity such that the exposure on the film is more uniform across the whole patient anatomy for optimal film brightness and contrast, and to reduce unnecessary x-ray radiation to thinner parts of the patient anatomy. With the system as disclosed herein, since only a portion of the patient anatomy is imaged at any one time, the compensation filter is typically not employed. Rather, the system can use the AEC (Automatic Exposure Control) to automatically adjust the x-ray output during long length imaging. In one embodiment, the AEC is used when acquiring each image of the exposure series.

Referring back to the operation sequence shown in FIG. 5, methods for image stitching step S140 are known to those skilled in the diagnostic imaging arts. As was described with reference to FIGS. 6 and 7, an overlap area P is typically used along the boundaries of image segments to be stitched in order to assist the stitching operation.

Figure 9A:
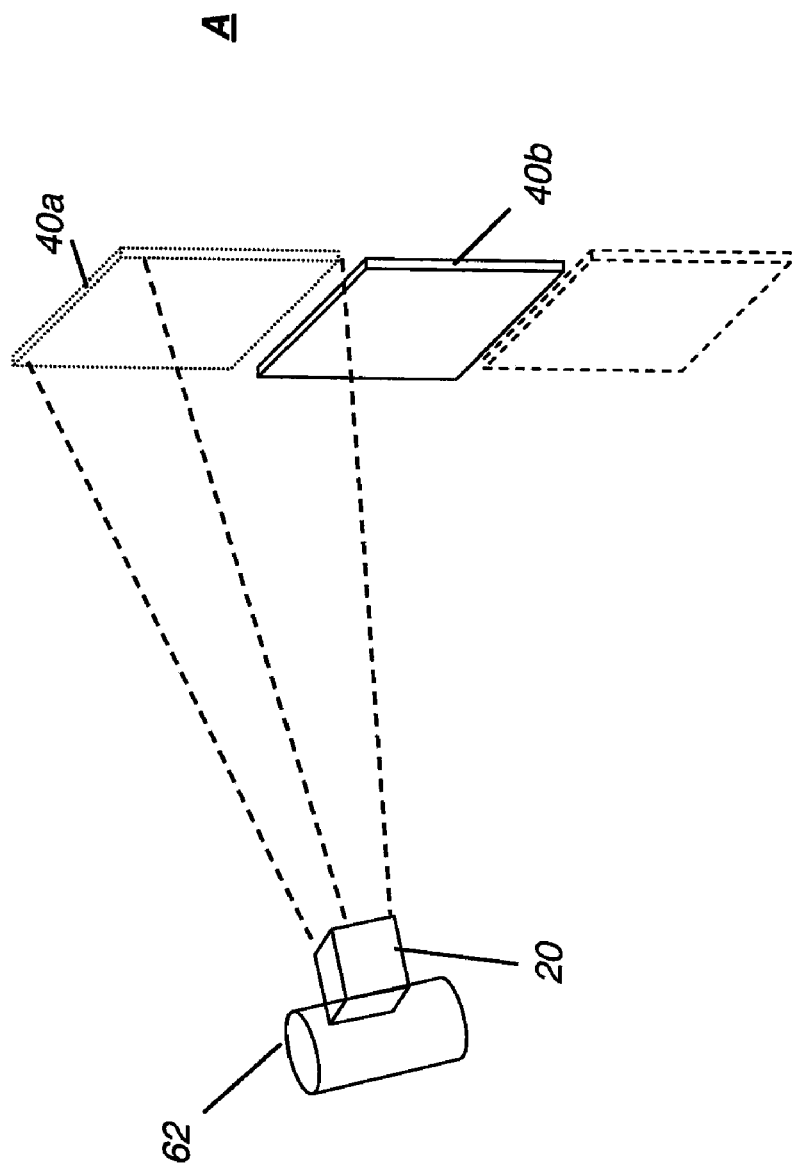
FIGS. 9A, 9B, and 9C are perspective views that show how detector translation apparatus and exposure directing apparatus cooperate to provide long-length imaging in an embodiment using two detectors to obtain three composite images.
Figure 9B:
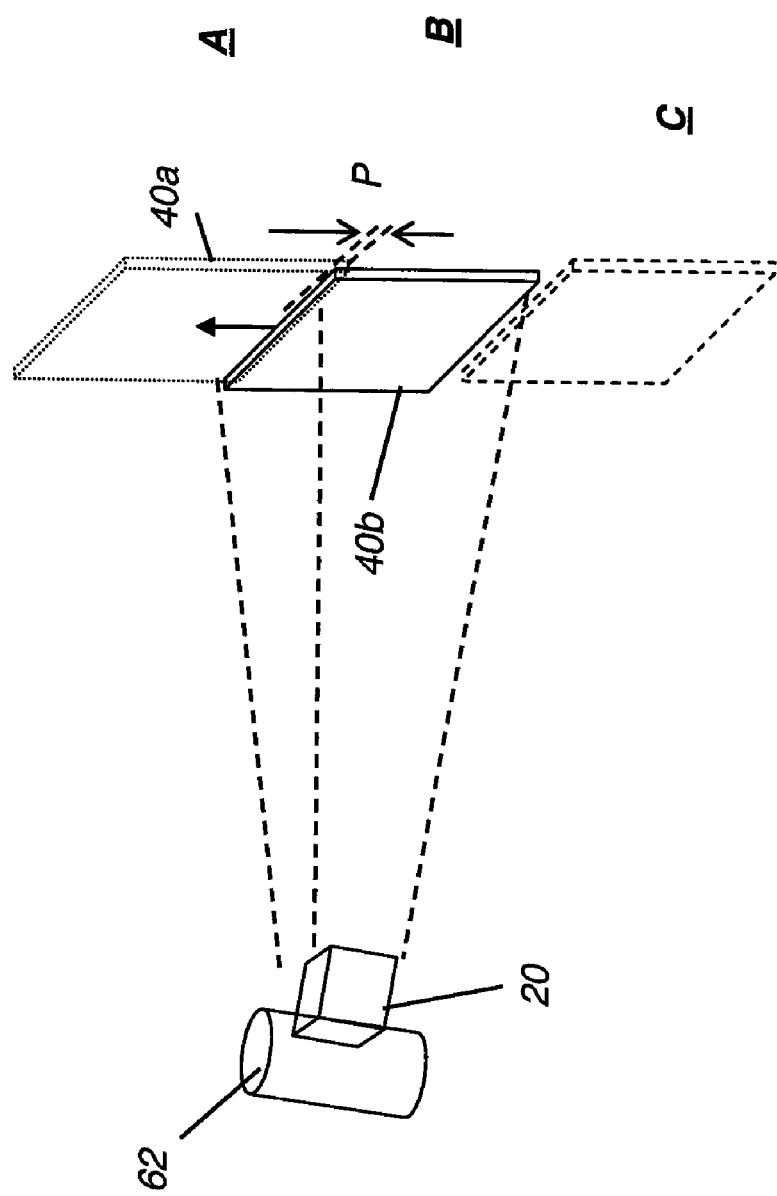
Figure 9C:
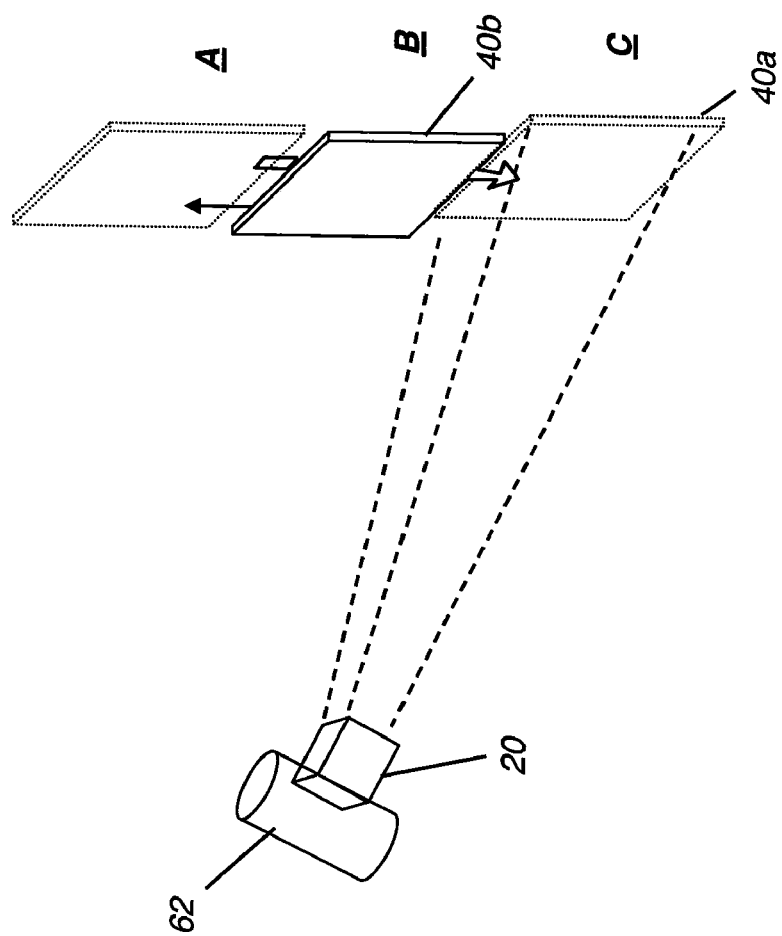

The embodiments shown earlier in FIGS. 3A-4B described long-length imaging for a composite image with two component images. The same basic approach, with interim positioning for the unused detector and appropriate translation of the DR detectors with an overlap along the boundary between imaging positions, can be extended to embodiments where three component images are needed from two x-ray detectors. FIGS. 9A, 9B, and 9C show a sequence of steps used for long-length imaging that obtain three component images to form a composite image, using two x-ray detectors. For this embodiment, x-ray detector 40a is exposed twice and must be a DR detector; detector 40b is exposed once and can be either a DR detector or a CR detector (or, with proper shielding used to block radiation when not being exposed, a film cassette). FIG. 9A shows the first exposure of DR x-ray detector 40a at imaging position A. FIG. 9B shows the second exposure, received by detector 40b at imaging position B. FIG. 9C then shows the third exposure at position C, again of DR x-ray detector 40a. The positioning and exposure steps are as follows, given by position:

Position A (FIG. 9A). DR x-ray detector 40a is exposed over its exposure interval at imaging position A. X-ray detector 40b is in a non-imaging interim position during this first exposure interval.

Position B (FIG. 9B). The exposed DR x-ray detector 40a is moved from position A, translated toward position C (dotted outline), in a downward direction in the vertical embodiment shown. The second x-ray detector 40b is translated in the opposite direction, upward by an increment, to imaging position B so that it overlaps imaging position A by the exposure overlap P. Exposure directing apparatus 62 is adjusted to direct exposure toward imaging position B. The image is then acquired over a second exposure interval at position B.

Position C (FIG. 9C). DR x-ray detector 40a has been translated from its initial position A toward position C. Before DR x-ray detector 40a is able to accept a second exposure (the third exposure in this series), the device must complete its data conversion and transfer the image data to the host processor, then perform an initializing refresh cycle to ready itself for a subsequent exposure. This processing can be performed while DR x-ray detector 40a is actively in motion. X-ray detector 40b is again incremented upward from its interim position used for the second exposure interval, to allow for another overlap distance P between imaging positions B and C. Exposure directing apparatus 62 is adjusted to direct exposure toward imaging position C. The image is acquired following the third exposure interval at position C.

The sequence of FIGS. 9A-9C benefits when DR x-ray detector 40a has a fast response and transfer time. For the sequence of FIGS. 9A-9C, detector translation apparatus 44 (FIGS. 1-4B) provides the mechanism for re-positioning x-ray detectors 40a and 40b in preparation for each image that is obtained. It should be noted that the general principles given in FIGS. 6 and 7 as to effective exposure length $L_d$ and overlap P apply for the sequence of FIGS. 9A-9C.

Figure 10:
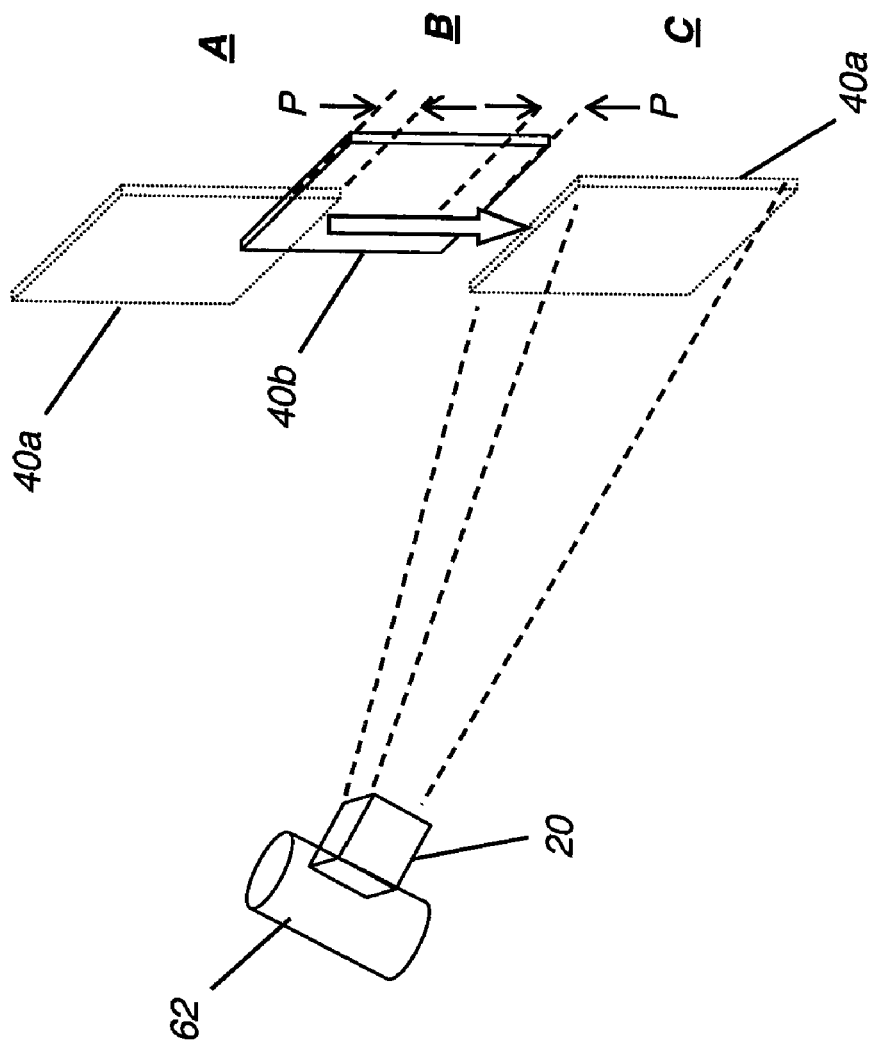
FIG. 10 is a perspective view that shows how detector translation apparatus and exposure directing apparatus cooperate to provide long-length imaging in an embodiment using two detectors to obtain three composite images in an alternate embodiment.

FIG. 10 shows the basic movement pattern of a sequence that is similar to that of FIGS. 9A-9C. In this embodiment, x-ray detector 40b is fixed in position for imaging at position B The movable DR x-ray detector 40a, shown in each of its imaging positions in FIG. 10, is then translated between imaging positions A and C, providing the required overlap distances and clearance for each imaging position. The positioning and exposure steps for one embodiment are as follows, given by position:

Position A. DR x-ray detector 40a is exposed at imaging position A. Position A overlaps position B by overlap P.

Position B. The exposed DR x-ray detector 40a is moved from position A, translated to an interim position that lies just past position C. The second x-ray detector 40b remains in place. Exposure directing apparatus 62 is adjusted to direct exposure toward imaging position B. The image is then acquired during this second exposure interval at position B.

Position C. Movable DR x-ray detector 40a is then translated upward from its interim position by an increment to position C, so that it overlaps position B by the exposure overlap P. Exposure directing apparatus 62 is adjusted to direct exposure toward imaging position C. The image is then acquired at imaging position C during a third exposure interval.

Movement of first and second DR detectors 40a and 40b between positions can be automatically initiated prior to the first exposure interval and following each exposure interval, or can be initiated manually by the technician, using a control button or other signal-providing device.

Advantageously, with the sequence of FIG. 10, second x-ray detector 40b is stationary. With respect to its initial position, only two moves are required for positioning first x-ray detector 40a.

A grid is generally recommended for improving contrast with various types of x-ray imaging. The apparatus and method of the present invention provide a number of alternatives for using a grid. In one embodiment, a full-length grid is provided behind the patient, such as part of a patient stand or other structure. Alternately, the individual x-ray detectors can each be provided with a grid or a grid cap.

The invention has been described in detail with particular reference to a presently preferred embodiment, but it will be understood that variations and modifications can be effected within the spirit and scope of the invention. For example, any of a number of types of motors or other actuators could be used for translating the positions of the x-ray detector or redirecting the exposure as part of exposure directing apparatus 62. Although the description and examples given in this disclosure show imaging arrangements having a vertical length direction, the same principles also apply where long-length imaging is performed along a horizontal or diagonal path or where the length direction lies along some other path.

Long-length imaging can be effected with the patient in the vertical or supine position, or other suitable position. Long-length imaging can also be done for living or inanimate objects, such as pipelines or other subjects that must be imaged and whose length or width exceeds the imageable dimensions of the DR detector.

The presently disclosed embodiments are therefore considered in all respects to be illustrative and not restrictive. The scope of the invention is indicated by the appended claims, and all changes that come within the meaning and range of equivalents thereof are intended to be embraced therein.

Parts List

12. Patient
20. X-ray source
30. Control circuitry
32. Operator console
40a, 40b. X-ray detector
44. Detector translation apparatus
48. Host processor
50. X-ray detector holder
60. Imaging apparatus
62. Exposure directing apparatus
68. Data link
80a, 80b. Image
90, 96. Stored settings
S100. Setup step
S110. X-ray exposure technique setup step
S120. Exposure and processing step
S130. Decision step
S134. Translation step
S140. hnage stitching step
S150. Image output step
S200. Initial setup step
S210. Storage step
S220. Looping step
S300. Initial setup step
S310. Storage step
S320. Looping step
A, B, C. Positions
$E_n$, $E_n'$. Exposure field size
$H_{top}$ Floor to top of radiation field;
$H_{bot}$ Floor to bottom of radiation field.
L. Exposure length
$L_d$. Effective exposure length
P. Exposure overlap
M. Offset distance

What is claimed is:

1. An apparatus for obtaining a long length x-ray image of a subject, comprising:
    a first x-ray detector comprising a first housing and a radiographic imaging array positioned within the first housing to receive incident radiation and output a signal corresponding thereto;
    a second x-ray detector comprising a second housing and a radiographic imaging array positioned within the second housing to receive incident radiation and output a signal corresponding thereto;
    an x-ray source having an exposure directing apparatus that is actuable to direct exposure from the x-ray source towards at least a first imaging position during a first interval and a second imaging position during a second interval, with an overlap along a boundary between the at least first and second imaging positions;
    an x-ray detector holder comprising a detector translation apparatus that is actuable to translate at least one of the first and second x-ray detectors along a length direction to an interim position for one of the first and second intervals and to either the first or the second imaging position for the other of the first and second intervals; and
    a host controller programmed to provide instructions for movement of the x-ray detector holder and exposure directing apparatus.

2. The apparatus of claim 1 wherein the detector translation apparatus is further actuable to move the first x-ray detector along the length direction to a third imaging position that overlaps an edge of the second imaging position relative to the length direction.

3. The apparatus of claim 1 wherein the exposure directing apparatus is further actuable to direct exposure from the x-ray source towards a third imaging position during a third interval and wherein the detector translation apparatus is further actuable to translate at least one of the first and second x-ray detectors to the third imaging position.

4. The apparatus of claim 1 wherein at least one of the first and second x-ray detectors is a digital radiography detector.

5. The apparatus of claim 1 wherein at least one of the first and second x-ray detectors is a computed radiography detector.

6. The apparatus of claim 1 wherein the exposure directing apparatus adjusts the angular orientation of the x-ray source.

7. The apparatus of claim 1 wherein the exposure directing apparatus adjusts the spatial position of the x-ray source.

8. The apparatus of claim 1 wherein the exposure directing apparatus adjusts an aperture in the path of exposure radiation.

9. The apparatus of claim 1 wherein the detector translation apparatus comprises a servo motor.

10. A method for obtaining a long length x-ray image of a subject, comprising:
    positioning a first x-ray detector in a first imaging position along a length direction and positioning a second x-ray detector in an interim position;
    exposing the first x-ray detector at the first imaging position;
    translating the second x-ray detector to a second imaging position that overlaps an edge of the first imaging position;
    exposing the second x-ray detector at the second imaging position;
    obtaining image data from the first and second x-ray detectors; and
    combining the obtained image data from the first and second x-ray detectors to form the long length x-ray image, where the second detector is separate and independent from the first detector.

11. The method of claim 10 wherein obtaining image data comprises adjusting a magnification factor to compensate for differences in distance between an x-ray source and the first and second x-ray detectors.

12. The method of claim 10 wherein exposing the second x-ray detector further comprises actuating an exposure directing apparatus that directs exposure from the x-ray source towards the second imaging position.

13. The method of claim 10 wherein at least one of the first and second x-ray detectors is a digital radiography detector.

14. The method of claim 10 wherein at least one of the first and second x-ray detectors is a computed radiography detector.

15. The method of claim 10 further comprising
    positioning the first x-ray detector in a third imaging position along the length direction; and exposing the first x-ray detector at the third imaging position.

16. A method for obtaining a long length x-ray image of a subject, comprising:
 positioning a first x-ray detector in a first imaging position along a length direction and positioning a second x-ray detector in a stationary position that defines a second imaging position, wherein the first imaging position overlaps the second imaging position;
 exposing the first x-ray detector at the first imaging position and obtaining image data from the first x-ray detector;
 translating the first x-ray detector out of the first imaging position;
 exposing the second x-ray detector at the second imaging position;
 translating the first x-ray detector to a third imaging position, wherein the third imaging position overlaps the second imaging position;
 exposing the first x-ray detector at the third imaging position;
 obtaining image data from the first and second x-ray detectors; and
 combining the obtained image data from the first and second x-ray detectors to form the long length x-ray image.

17. The method of claim 16 wherein at least the first x-ray detector is a digital radiography detector.

18. The method of claim 16 wherein the second x-ray detector is a computed radiography detector.

19. A method for obtaining a long length x-ray image of a subject, comprising:
 disposing a first x-ray detector comprising a first housing and a radiographic imaging array positioned within the first housing in a first imaging position along a length direction;
 directing x-rays to the first imaging position to expose the first x-ray detector;
 translating either the first x-ray detector, or a second x-ray detector comprising a separate second housing and a radiographic imaging array positioned within the second housing, or both the first and second x-ray detectors, to dispose the second x-ray detector in a second imaging position that overlaps an edge of the first imaging position;
 directing x-rays to the second imaging position to expose the second x-ray detector;
 obtaining image data from the first and second x-ray detectors; and
 combining the obtained image data from the first and second x-ray detectors to form the long length x-ray image.

20. The method of claim 19 further comprising translating the first x-ray detector to a third imaging position that overlaps an edge of the second imaging position and directing x-rays to the third imaging position to expose the first x-ray detector.

* * * * *